United States Patent [19]

Amemura et al.

[11] Patent Number: 5,118,622

[45] Date of Patent: Jun. 2, 1992

[54] POLYPEPTIDE POSSESSING ISOAMYLASE ACTIVITY, AND ITS USE IN THE HYDROLYSIS OF AMYLACEOUS SUBSTANCES

[75] Inventors: Akinori Amemura; Masamitsu Futai, both of Osaka, Japan

[73] Assignee: Kabushiki Kaisha Hayashibara Seibutsu Kagaku Kenkyujo, Okayama, Japan

[21] Appl. No.: 305,974

[22] Filed: Feb. 3, 1989

[30] Foreign Application Priority Data

Feb. 4, 1988 [JP] Japan .................................. 63-24762

[51] Int. Cl.$^5$ .......................... C12N 9/44; C12P 19/22
[52] U.S. Cl. ...................................... 435/210; 435/95; 435/874
[58] Field of Search .......................... 435/95, 210, 874; 426/42

[56] References Cited

U.S. PATENT DOCUMENTS 3,560,345  2/1971  Yokohayashi et al. .
3,795,584  3/1974  Mitsuhashi et al. .
4,028,186  6/1977  Sakai .
4,032,403  6/1977  Sakai et al. .
4,408,041  10/1983  Hirao et al. .

FOREIGN PATENT DOCUMENTS 959782  12/1974  Canada .
3938    1/1979   Japan .
28153   6/1981   Japan .
28154   6/1981   Japan .
3356    1/1982   Japan .
134498  8/1982   Japan .
23799   2/1983   Japan .

OTHER PUBLICATIONS

Kato, K. et al., "Affinity Chromatography of *Pseudomonas isoamylase* on Cross-Linked Amylose Gel", *Agric. Biol. Chem.* 41(10)p. 2077-2080, 1977.
Amemuras A., "Molecular Weight of the Undergraded Polypeptide Chain of *Pseudomonas Amylderamosa* Isoamylase"*Biochemica at Biophysica Acta*, 611 (1980) pp. 390-393.
Tognoni, A. et al., "Cloning and Nucleotide Sequence of the Isoamylase Gene" from a Strain of *Pseudomonas sp. J. of Gen. Microbiol.* 135, pp. 37-45, 1989.
Amemura, A. et al., "Cloning and Nucleotide Sequence of the Isoamylase Gene" from *Pseudomones amyloderamosa* 28-15, *J. Biol. Chem.*, 263:19 pp. 9271-9276, Jul. 1988.
Harada, T., "Isoamylase and its Industrial Significance in the Production of Sugars from Starch", *Biotechnology and Gen. Engin. Reviews*, pp. 39-63, 1984.
Applied Microbiology, vol. 16, No. 1, (1968), pp. 1439-1444, "Formation of Isoamylase by Pseudomonas" by Tokuya Harada et al.
Applied Microbiology, vol. 28, No. 3, (1974), pp. 336-339, "Formations of Extracellular Isoamylase and Intracellular α-Glucosidase and Amylase(s) by Pseudomonas SB15 and a Mutant Strain" by Toshiyuki Sugimoto, et al.
FEBS Letters, vol. 57, No, 1, (1975), pp. 1-4, "Identification of Isoamylase, A Glycogen-Debranching Enzyme, from *Bacillus Amyloliquefaciens*" by Herbert Urlaub and Gunter Wober.

(List continued on next page.)

*Primary Examiner*—Douglas W. Robinson
*Assistant Examiner*—Manan C. Knode
*Attorney, Agent, or Firm*—Browdy and Neimark

[57] ABSTRACT

A polypeptide possessing isoamylase activity with a revealed amino acid sequence. The polypeptide has features that it acts on amylaceous substances to produce a high-maltose content product, and that it has a molecular weight of 80,000±5,000 daltons on SDS-polyacrylamide gel electrophoresis, as well as having an isoelectric point of 4.7±0.1 on polyacrylamide gel isoelectric electrophoresis.

The polypeptide can be advantageously used in the industrial manufacture of starch syrups.

8 Claims, 1 Drawing Sheet

OTHER PUBLICATIONS

Starch/Stärke 32 No. 4, (1980), pp. 132–136, "Purification and Characterization of Extracellular Isoamylase from Flavobacterium sp." by H. H. Sato and Y. K. Park.

Applied and Environmental Microbiology, vol. 44, No. 6 (1982), pp. 1253–1257, "Extracellular Isoamylase Produced by the Yeast *Lipomyces kononenkoae*" by Isabel *Spencer-Martins.*

Gene, 19, (1982), pp. 259–268, "The pUC plasmids, an M13mp7-derived system for insertion mutagensis and sequencing with synthetic universal primers (Recombinant DNA; multiple cloning sites; restriction sites mobilizing element; dideoxy sequencing)" by Jeffrey Vieria and Joachim Messing.

The Journal of Biological Chemistry, vol. 256, No. 15, (1981), pp. 7990–7997, "A Gas-Liquid Solid Phase Peptide and Protein Sequenator" by Rodney M. Hewick, et al.

Journal of Bacteriology, vol. 127, No. 3, (1976), pp. 1524–1537, "Motility as a Morphogenic Character in the Genus Arthrobacter" by G. J. Stanlake and J. B. Clark, and Simple Agarose Gel Electrophoretic Method for the Identification and Characterization of Plasmid Deoxyribonucleic Acid by Jane Aldrich Meyers, et al.

Journal of Molecular Biology, vol. 98, (1975), pp. 503–517, "Detection of Specific Sequences Among DNA Fragments Separated by Gel Electrophoresis" by E. M. Southern.

The Journal of Biological Chemistry, vol. 244, No. 16, (1969), p. 4406, "The Reliability of Molecular Weight Determinations by Dodecyl Sulfate-Polyacrylamide Gel Electrophoresis" by Klause Weber and Mary Osborn.

Journal of Bacteriology, vol. 169, No. 5, (1987), pp. 2301–2306, "Entire Nucleotide Sequence of the Pullulanase Gene of *Klebsiella aerogenes* W70" by Nobuhiro Katsuragi, et al.

POLYPEPTIDE POSSESSING ISOAMYLASE ACTIVITY, AND ITS USE IN THE HYDROLYSIS OF AMYLACEOUS SUBSTANCES

BACKGROUND OF THE INVENTION

Field of the Invention

The present invention relates to a polypeptide possessing isoamylase activity, and a process for preparing a high-maltose content product by subjecting an amylaceous substance to the action of the polypeptide together with a beta-amylase.

Abbreviations

In the specification, amino acids, peptides, etc., may be abbreviated to the names which are commonly used in the art. Some of such abbreviations are given in the below. Optical isomers of amino acids represented by such abbreviations are in L-configuration unless otherwise specified.

DNA: deoxyribonucleic acid
RNA: ribonucleic acid
A: adenine
T: thiamine
G: guanine
C: cytocine
dNTP: deoxynucleotide triphosphate
ddNTP: dideoxynucleotide triphosphate
dCTP: deoxycytidin triphosphate
SDS: sodium dodecyl sulphate
Ala: alanine
Arg: arginine
Asn: asparagine
Asp: aspartic acid
Cys: cysteine
Gln: glutamine
Glu: glutamic acid
Gly: glycine
His: histidine
Ile: isoleucine
Leu: leucine
Lys: lysine
Met: methionine
Phe: phenylalanine
Pro: proline
Ser: serine
Thr: threonine
Trp: tryptophan
Tyr: tyrosine
Val: valine

DESCRIPTION OF THE PRIOR ART

As described, for example, in *Applied Microbiology*, Vol. 16, pp. 1439-1444 (1968), and ibid , Vol. 28, No. 3, pp. 336-339 (1974), it has been known that an enzyme, which hydrolyzes alpha-1,6-glucosidic linkages of starch and i.e., isoamylase (EC 3.2.1.68), is produced by a microorganism of the species *Pseudomonas amyloderamosa*, a microorganism of the genus Cytophaga described in *FEBS Letters*, Vol. 57, No. 1, pp. 1-4 (1975), a microorganism of the genus Flavobacterium described in *Starch/Starke*, Vol. 32, No. 4, pp. 132-136 (1980), or a microorganism of the species *Lipomyces kononenkoae* described in *Applied and Environmental Microbiology*, Vol. 44, No. 6, pp. 1253-1257 (1982).

These prior art references only teach a part of the enzymatic properties, and such teaching is not enough to use isoamylase in terms of consistent industrial supply and uses. Thus, a much greater development of isoamylase supply has been in great demand.

SUMMARY OF THE INVENTION

The present inventors studied an isoamylase, and, specifically, a polypeptide possessing isoamylase activity, and have revealed its amino acid sequence, and its uses. The polypeptide possessing isoamylase activity will hereinafter be referred to as "polypeptide".

As a result, the present inventors found that the polypeptide comprises either or both partial amino acid sequences selected from the group consisting of (a) Met—Asp—Val—Val—Tyr—Asn—His—Thr, and (b) Asp—Gly—Phe—Arg—Phe—Asp—Leu and, more particularly, that these partial amino acid sequences are located in this order with respect to the N-terminal of the polypeptide.

The polypeptide has a characteristic property of hydrolyzing alpha-1,6-glucosidic linkages of starch and glycogen.

The present invention and its effects will herein-after be explained.

BRIEF DESCRIPTION OF THE ACCOMPANYING DRAWING

Figure shows a restriction map of recombinant DNA pIAM275 carrying a polypeptide gene derived from *Pseudomonas amyloderamosa* SB-15 (ATCC 21262).

DETAILED DESCRIPTION OF THE INVENTION

Figure 1:
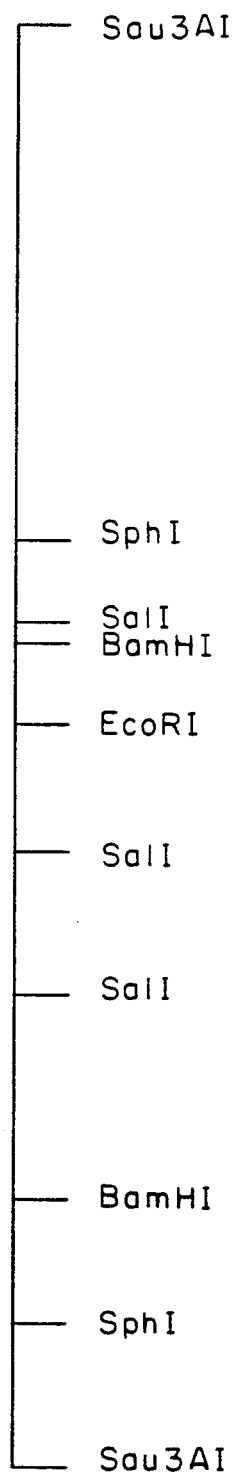

In the present invention, the amino acid sequence of the polypeptide was determined first by cloning a polypeptide gene in an isoamylase producing microorganism, then decoding the polypeptide gene.

The amino acid sequence containing the N-terminal was determined by purifying the polypeptide substantially to homogeneity, and subjecting it to a gas-phase protein sequencer.

CLONING OF POLYPEPTIDE GENE

A DNA component is isolated from a donor microorganism capable of producing the polypeptide, and purified, for example, with ultrasonic or restriction enzymes to obtain a DNA fragment. The obtained DNA fragment and a vector fragment, obtained by cleaving a vector in the same manner, are ligated, for example, with a DNA ligase to obtain a recombinant DNA carrying the polypeptide gene.

The donor microorganism is chosen from polypeptide producing microorganisms. Examples of such microorganisms include *Pseudomonas amyloderamosa* ATCC 21262 described in the U.S. Pat. No. 3,560,345, or its mutants.

A DNA component can be prepared by culturing a donor microorganism, for example, with a liquid culture medium for about 1-3 days under agitation-aeration conditions, centrifugally separating the cells from the culture, and lysing the cells with procedures. Examples of such procedures are enzymatic treatment, for example, lysozyme- or beta-glucanase-treatment, and ultrasonic treatment. Other enzymes such as protease, surface-active agent such as sodium lauryl sulfate and/or freezing-thawing treatment can be freely used in combination, if necessary.

In order to isolate and purify DNA from the resultant lysate, two or more conventional procedures such as phenol extraction, protein removal, protease treatment, ribonuclease treatment, alcohol sedimentation, and centrifugation can be used in combination.

Although cleavage of DNA can be effected, for example, by treating it with ultrasonication or restriction enzymes. The use of restriction enzymes, in particular, Type II restriction enzymes, for example, Sau3AI, EcoRI, HindIII, BamHI, SalI, XmaI, XbaI, SacI and PstI that act on a specific nucleotide sequence, enables smooth ligation of the cleaved DNA- and vector-fragments.

Bacteriophages and plasmids which autonomically proliferate in a host microorganism are suitable for a vector.

When a microorganism of the species Escherichia coli is used as the host, bacteriophages such as λgt.λC and λgt.λB are employable, while ρ11, ψ1 and ψ105 are usable when a microorganism of the species Bacillus subtilis is used as the host.

As regards plasmids, when a microorganism of the species Escherichia coli is used as the host, plasmids such as pBR322 and pUC18 are employable, while pUB110, pTZ4 (pTP4) and pC194 are usable for a host microorganism of the species Bacillus subtilis. Plasmids, for example, pHV14, TRp7, YEp7 and pBS7, which autonomically proliferate in two or more different host microorganisms such as Escherichia coli and Bacillus subtilis, can be used as a vector. These vectors are cleaved with a restriction enzyme similarly as in cleavage of DNA to obtain a vector fragment.

DNA- and vector-fragments are ligated with conventional procedure using a DNA ligase. For example, DNA- and vector-fragments are first annealed, then subjected in vitro to the action of a suitable DNA ligase to obtain a recombinant DNA. If necessary, such recombinant DNA can be prepared by introducing the annealed fragments into a host microorganism, and subjecting the annealed fragments in vivo to a DNA ligase.

The host microorganisms usable in the invention are those in which the recombinant DNA autonomically and consistently proliferates to express its characteristics.

The recombinant DNA can be introduced into a host microorganism with a conventional procedure. For example, when a host microorganism belongs to the species Escherichia coli, introduction of recombinant DNA is effected in the presence of calcium ion, while the competent cell- and protoplast-methods are employable when a host microorganism of the genus Bacillus is used.

A transformed microorganism in which a recombinant DNA has been introduced is selected by colony hybridization method using oligonucleotide labelled with $^{32}$P, or by collecting clone(s) which grows on a plate culture containing starch to convert starch into amylose.

The present inventors found that the recombinant DNA carrying the polypeptide gene could be cleaved with a restriction enzyme to obtain a DNA fragment carrying the polypeptide gene which was then easily ligated with a vector fragment which had been obtained by splicing a vector such as plasmid in the same manner.

SEQUENCE OF THE POLYPEPTIDE GENE

The polypeptide gene is decoded by the chain-terminator method described in Gene, Vol. 19, pp. 259-268 (1982).

In this method, a DNA fragment carrying a cloned polypeptide gene is inserted into a cloning site of a plasmid such as pUC18 with a restriction enzyme. The obtained recombinant plasmid is introduced by transformation into a suitable strain of the species Escherichia coli such as Escherichia coli JM83, followed by selection of a microorganism containing the recombinant plasmid.

Such microorganism is proliferated and then used to prepare a recombinant plasmid.

The obtained recombinant plasmid is annealed together with a synthetic primer, and Klenow fragment is then allowed to act on the annealed product to extend the primer. Thus, a complementary DNA is obtained.

Thereafter, the reaction mixture is subjected sequentially to polyacrylamide gel electrophoresis and radio-autography, followed by determination of polypeptide gene.

The sequence of a signal peptide which triggers off extracellular secretion of polypeptide can be determined in the same manner.

AMINO ACID SEQUENCE OF THE POLYPEPTIDE

An amino acid sequence of the polypeptide is determined with the DNA sequence of the polypeptide gene.

An amino acid sequence of a signal peptide which triggers off extracellular secretion of polypeptide can be determined in the same manner.

PARTIAL AMINO ACID SEQUENCE CONTAINING N-TERMINAL THE OF POLYPEPTIDE

A polypeptide producing microorganism of the species Pseudomonas amyloderamosa is cultured with a nutrient culture medium to produce a polypeptide. After completion of the culture, the supernatant, centrifugally separated from the culture, is purified by ammonium sulfate fractionation, ion-exchange chromatography and high-performance liquid chromatography to obtain a high-purity polypeptide specimen. The specimen is then degraded with a gas-phase protein sequencer in accordance with the method described in The Journal of Biological Chemistry, Vol. 256, No. 15, pp. 7990-7997 (1981) with high-performance liquid chromatography, and determined for its partial amino acid sequence containing N-terminal.

PREPARATION OF THE POLYPEPTIDE WITH A TRANSFORMED MICROORGANISM

The present inventors found that a large amount of the polypeptide can be consistently produced by culturing a transformed microorganism with a nutrient culture medium.

Into the nutrient culture medium is incorporated, for example, carbon source, nitrogen source, minerals, and, if necessary, a small amount of organic nutrient such as amino acid and vitamin.

Starch, partial starch hydrolysate, and saccharides such as glucose, fructose, sucrose and maltose are suitable for the carbon sources. Inorganic nitrogen sources such as ammonia gas, ammonia water, ammonium salts and nitrates; and organic nitrogen sources such as peptone, yeast extract, defatted soybean meal, corn steep liquor and meat extract are suitable for the nitrogen sources.

Cultivation of a transformed microorganism is carried out with a nutrient culture medium for about 1-6 days under aerobic conditions such as agitation-aeration conditions to accumulate polypeptide while keeping the nutrient culture medium, for example, at pH 2-8 and 25°-65° C.

Although the polypeptide in the resultant culture may be used intact, generally, the culture is separated into a polypeptide solution and cells with a conventional procedure such as filtration and centrifugation, prior to its use.

Cells which have polypeptide intracellularly are treated with ultrasonic, surface-active agent and/or cytohydrolytic enzyme, and the resultant is filtered and centrifuged to obtain a polypeptide solution.

The polypeptide solution is purified by appropriately combining, for example, with concentration in vacuo, concentration using membrane filter, adsorption and elution using starch, salting-out using ammonium sulfate or sodium sulfate, and fractional sedimentation using methanol, ethanol or acetone into a much more homogenous form, prior to its use. The obtained polypeptide can be advantageously used when immobilized by conventional methods such as carrier-linkage, cross-linkage and entrapment.

The polypeptide usable in the present invention should not be restricted to one derived from the above described transformed microorganism, as long as it has been elucidated that polypeptide has a specified amino acid sequence and is safely usable.

Since the polypeptide can be favorably used to hydrolyze alpha-1,6-glucosidic linkages of amylopectin and glycogen, the polypeptide can be favorably used in a process for preparing an amylose from amylaceous substances such as starch, amylopectin and partial starch hydrolysate.

Furthermore, the polypeptide can act on the amylaceous substances in order to facilitate a preparation of a high-glucose content product or a high-maltose content product together with the action of glucoamylase or a beta-amylase.

For example, a high-maltose content product can be prepared by subjecting a gelatinized- or liquefied-starch described in U.S. Pat. No. 3,795,584 or Canadian patent 882,703, to the action of an isoamylase in combination with a beta-amylase.

Furthermore, the maltose content in the above product can be effected by subjecting contaminating saccharides such as maltotriose which are present in the above high-maltose content product, to the action of one or more enzymes described in U.S. Pat. No. 4,032,403 and 4,028,186, or by chromatographing the contaminating saccharides with a strongly-acidic cation-exchange resin described in Japanese Patent Laid-Open No. 23,799/83.

Thereafter, the obtained high-maltose content product is usually filtered, purified with decoloration using activated charcoal and deionization using ion-exchange resins in H- and OH-form, and concentrated into a syrup which is then added with a seed crystal of maltose to effect crystalization. The resultant product can be pulverized, or separated to obtain the highest possible purity of maltose.

The resultant maltose can be extensively used in foods as a sweetener, as well as in pharmaceuticals as a saccharide for injections and nutrient supplements.

Furthermore, the maltose can be hydrogenated by the method described in U.S. Pat. No. 4,408,041 into a maltitol which can be favorably used as a non-assimilable sweetener, health food and diet food.

Detailed description of the present invention will hereinafter be explained by the following Experiments.

EXPERIMENT 1

Cloning of *Pseudomonas amyloderamosa* polypeptide gene into *Escherichia coli*

Experiment 1-(1)

Preparation of Chromosome DNA Carrying Polypeptide Gene of *Pseudomonas amyloderamosa*

A seed culture of *Pseudomonas amyloderamosa* SB-15 (ATCC 21262) was cultured with a culture medium containing 1 w/v % peptone, 0.5 w/v % yeast extract and 0.5 w/v % sodium chloride at 30° C. under agitation-aeration conditions. Cells, centrifugally separated from the culture, were suspended with Tris buffer (pH 8.0) containing 25 w/v % sucrose, added with lysozyme to give 0.15 w/v %, and incubated at 25° C. for 20 minutes. The incubated mixture was added with ethylenediaminetetraacetic acid (EDTA) to give 62.5 mM, and the mixture was incubated for 20 minutes, added with SDS to give 0.0625 w/v %, and heated to 57° C. to complete cytohydrolysis.

The resultant solution was treated with RNase A (a ribonuclease) and Pronase K (a protease) which were commercialized by Boehringer Mannheim GmbH, Germany. The resultant was added with a mixture of chloroform and isoamylalcohol. The resultant mixture was centrifuged to obtain a supernatant which was then added with 2 volumes of ethanol to recover a chromosome DNA, and dissolved in SSC buffer containing sodium chloride and trisodium citrate. The resultant chromosome DNA was treated with a solution containing chloroform and isoamylalcohol, precipitated with ethanol, and then precipitated with isopropanol to obtain a purified chromosome DNA.

Experiment 1-(2)

Preparation of Plasmid pUC9

Plasmid pUC9 was isolated and prepared from a microorganism of the species *Escherichia coli* in accordance with the method described by J. Meyers et al. in *Journal of Bacteriology*, Vol. 127, No. 3, pp. 1529-1537 (1976).

Experiment 1-(3)

Preparation of Recombinant DNA Carrying Polypeptide Gene

The purified chromosome DNA carrying polypeptide gene, prepared in Experiment 1-(1), was partially digested with Sau3AI, a restriction enzyme commercialized by Takara Shuzo Co., Ltd., Kyoto, Japan, and separated with sucrose density gradient ultracentrifugation to give a chromosome DNA fragment of about 3-7 kbp. A plasmid vector pUC9 which had been digested with Bam HI, a restriction enzyme commercialized by Takara Shuzo Co., Ltd., Kyoto, Japan, was mixed with the chromosome DNA fragment of about 3-7 kbp, and the mixture was added with T4 DNA ligase commercialized by Toyobo Co., Ltd., Tokyo, Japan, and ligated at 4° C. overnight to obtain a recombinant DNA.

Experiment 1-(4)

Selection of Recombinant DNA Possessing Polypeptide Gene

A seed culture of *Escherichia coli* JM83 (ATCC 35607) as the host microorganism was cultured with YT-broth containing 0.8 w/v % tryptone, 0.5 w/v % yeast extract and 0.25 w/v % sodium chloride, at 37° C. for 75 minutes. Cells, centrifugally separated from the culture, were suspended with an aqueous solution of 50 mM calcium chloride, cooled in an ice-chilled water bath for 40 minutes, centrifugally separated again, resuspended with an aqueous solution of 50 mM calcium chloride, added with the recombinant DNA prepared in Experiment 1-(3), and cooled in an ice-chilled water bath for 60 minutes. The mixture was then warmed to 42° C., added with YT-broth, incubated at 37° C. for 90 minutes, centrifugally separated, suspended with 0.85 w/v % sodium chloride, spread on a medium containing 5-bromo-4-chloro-3-indoly-$\beta$-galactoside or X-gal, and cultured to form white colonies which were then isolated as recombinant microorganisms. The obtained about 100 colonies were fixed on a nitro cellulose plate. Thirteen strains which had been smoothly aggregated at 30° C. with a probe which had been prepared by labeling a recombinant DNA corresponding to bases 1–16 from the N-terminal of the polypeptide, i.e.,

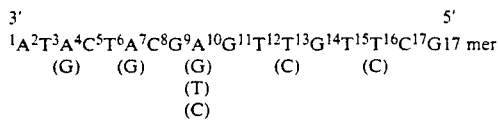

(wherein the third base is A or G; the sixth base, A or G: the ninth base, A, G, T or C; the twelfth base, T or C; and the fifteenth base, T or C: and it gives a mixture of 64 recombinant DNAs) with $^{32}P$ were chosen.

A strain which was also aggregated with a recombinant DNA probe corresponding to bases 15–19 from the N-terminal of the polypeptide, i.e.,

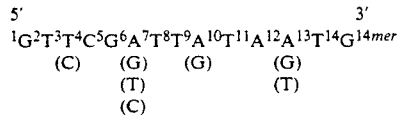

(wherein the third base is T or C; the sixth, A, G, T or C; the ninth base, A or G; and the twelfth base, A, G or T; and a mixture of 48 recombinant DNAs) was chosen from the above 13 strains by using the Southern method described in *Journal of Molecular Biology*, Vol. 98, page 503–517 (1975).

A microorganism of the strain and its recombinant DNA were named "*Escherichia coli* IAM275" and "pIAM275", respectively.

The restriction map of recombinant DNA pIAM275, in particular, that of the DNA fragment derived from *Pseudomonas amyloderamosa* is shown in Figure.

The length of the DNA as shown in Figure is 5.5 kbp.

Experiment 2

Partial amino acid sequence containing N-terminal of *Pseudomonas amyloderamosa* polypeptide Experiment 2-(1)

Preparation of Polypeptide

A seed culture of *Pseudomonas amyloderamosa* SB-15 (ATCC 21262) was cultured with a culture medium (pH 7.0) containing 2 w/v % maltose, 0.4 w/v sodium glutamate, 0.15 w/v % ammonium phosphate, 0.1 w/v % dipotassium phosphate, 0.05 w/v % magnesium sulfate hepta hydrate, 0.0001 w/v % iron chloride hexa hydrate and 0.0001 w/v % manganase chloride at 30° C. for 3 days under agitation-aeration conditions to produce a polypeptide in the culture medium.

The culture medium was centrifugally separated to obtain a supernatant. A polypeptide fraction was precipitated from the supernatant with ammonium sulfate, purified by chromatographing using "DEAE-cellulose", an anion exchanger, a product of Brown Company, USA, and "CM-cellulose", a cation exchanger, a product of Wako Pure Chemical Industries, Ltd., Osaka, Japan, to obtain a high-purity polypeptide specimen.

On SDS-polyacrylamide gel electrophoresis in accordance with the method described by K. Weber and M. Osborn in *Journal of Biological Chemistry*, Vol. 244, page 4,406 (1969), the polypeptide specimen showed a molecular weight of 80,000±5,000 daltons The polypeptide specimen showed an isoelectric point of 4.7±0.1 on polyacrylamide gel isoelectric electrophoresis using "AMPHOLINE PAGPLATE (pH 3.5–9.5)", a product of LKB-Produkter AB, Stockholm, Sweden.

The specific activity of the polypeptide specimen was 59,000±5,000 units/mg protein.

One unit of the isoamylase activity was defined as the amount of enzyme that increased the absorbance by 0.01/h at 610 nm. The procedure was carried out as follows: Five milliliters of 1.0 w/v % soluble glutinous rice starch was added with 1 ml of 0.5M acetate buffer (pH 3.5), added with 1 ml of an enzyme solution, and the mixture was incubated at 40° C. for a prescribed period to effect enzymatic reaction. Thereafter, 1 ml of the reaction mixture was added with 1 ml of 0.01M iodine solution containing iodine and potassium iodide. The resultant mixture was diluted with water to give 25 ml, and reacted for 15 minutes. The reaction mixture was placed in a cell, 1 cm in depth, and measured its absorbance at 610 nm.

Experiment 2-(2)

Partial Amino Acid Sequence Containing N-Terminal of Polypeptide

A polypeptide specimen, prepared by the method in Experiment 2-(1), was fed to "Model 470A", a gas-phase protein sequencer commercialized by Applied Biosystems Inc., Calif., USA, and then analyzed with high-performance liquid chromatography to determine a partial amino acid sequence containing N-terminal of the polypeptide.

The partial amino acid sequence was Ala—Ile—Asn—Ser—Met—Ser—Leu—Gly—Ala—Ser—Tyr—Asp—Ala—Gln—Ala—Asn—Ile—Thr—Phe.

EXPERIMENT 3

Sequence of Polypeptide Gene Derived from *Pseudomonas Amyloderamosa* and Amino Acid Sequence of Polypeptide Experiment 3-(1)

Preparation of plasmid pUC18

Plasmid pUC18 was prepared in accordance with the method in Experiment 1-(2) from *Escherichia coli* JM83 in which the plasmid had been introduced.

Experiment 3-(2)

Preparation of Recombinant DNA Carrying Polypeptide Gene

A recombinant DNA was prepared by the method in Experiment 1-(3).

A plasmid carrying polypeptide gene prepared by the method in Experiment 1-(2) was cleaved by restriction enzymes to prepare a fragment carrying polypeptide gene, and a plasmid pUC18 prepared by the method in Experiment 3-(1) was cleaved by restriction enzymes in the same manner to prepare a fragment. These fragments were subjected to T4 DNA ligase to obtain a recombinant DNA.

Experiment 3-(3)

Introduction of Recombinant DNA into *Escherichia Coli*

*Escherichia coli* JM83 was transformed by incorporating the recombinant DNA into it according to the method in Experiment 1-(4).

Experiment 3-(4)

Preparation of Recombinant DNA From Transformed Microorganism

A transformed microorganism was cultured with L-broth containing 50 μg/ml of ampicillin, and the obtained cells were then lysed with alkali to obtain a recombinant DNA.

Experiment 3-(5)

Sequence of Recombinant DNA

The recombinant DNA was decoded by the dideoxy chain terminator method.

The recombinant DNA, prepared in Experiment 3-(4), and a synthetic primer composed of 17 bases were mixed, annealed at 60° C. for 20 minutes, added with dNTP, ddNTP, ($\alpha$-$^{32}$P) dCTP and Klenow fragment, and reacted at 37° C. for 30 minutes to extend the primer towards the 3′ site from the 5′ site. Thus, a complementary DNA was obtained. To the complementary DNA was added an excessive amount of dNTP, and the mixture was reacted at 37° C. for 30 minutes, followed by addition of a dye mixture in formamide to suspend the reaction. The reaction mixture was boiled for 3 minutes, and electrophoresed on 6% polyacrylamide gel at about 25 mA to separate an extended complementary DNA. After completion of the electrophoresis, the gel was fixed and dehydrated.

The dehydrated gel was then autoradiographed, and the polypeptide gene was determined by analyzing base bands on the radioautogram.

The results were as shown in Table 1-1.

The signal peptide gene located upstream the 5′-terminal of the polypeptide gene was decoded in the same manner.

The results were as shown in Table 1-2.

TABLE 1-1

| 10 | 20 | 30 | 40 | 50 | 60 |
|---|---|---|---|---|---|
| GCCATCAACA | GCATGAGCCT | GGGCGCGAGC | TACGACGCGC | AACAGGCCAA | CATCACCTTT |
| 70 | 80 | 90 | 100 | 110 | 120 |
| CGCGTTTACT | CCTCGCAGGC | CACGCGCATC | GTGCTGTACC | TCTATTCGGC | AGGTTACGGT |
| 130 | 140 | 150 | 160 | 170 | 180 |
| GTGCAGGAGT | CGGCCACCTA | CACGCTGAGC | CCAGCGGGCA | GTGGTGTATG | GGCGGTGACG |
| 190 | 200 | 210 | 220 | 230 | 240 |
| GTGCCGGTGT | CGTCGATCAA | GGCGGCCGGC | ATCACGGGGG | CGGTGTACTA | CGGGTATCGC |
| 250 | 260 | 270 | 280 | 290 | 300 |
| GCCTGGGGGC | CGAATTGGCC | TTATGCCAGC | AACTGGGGCA | AGGGTTCGCA | GGCGGGCTGT |
| 310 | 320 | 330 | 340 | 350 | 360 |
| GTTTCCGACG | TCGACGCCAA | CGGCGACCGC | TTCAATCCCA | ACAAACTGTT | GTTGGACCCC |
| 370 | 380 | 390 | 400 | 410 | 420 |
| TACGCGCAGG | AAGTGAGCCA | GGATCCGCTG | AACCCGTCCA | ACCAGAACGG | CAACGTGTTC |
| 430 | 440 | 450 | 460 | 470 | 480 |
| GCCTCTGCGC | ACTATCGCAC | CACCGACAGT | GGCATCTATG | CACCCAAGGG | TGTCGTGCTG |
| 490 | 500 | 510 | 520 | 530 | 540 |
| GTGCCCAGTA | CGCAAAGTAC | CGGCACCAAA | CCCACACGCG | CGCAGAAGGA | TGATGTGATC |
| 550 | 560 | 570 | 580 | 590 | 600 |
| TACGAGGTGC | ATGTGCGCGG | CTTCACCGAG | CAGGACACCT | CTATCCCTGC | GCAGTATCGC |
| 610 | 620 | 630 | 640 | 650 | 660 |
| GGCACCTATT | ACGGTGCAGG | GCTCAAGGCC | AGTTACCTCG | CCAGCCTGGG | CGTGACCGCG |
| 670 | 680 | 690 | 700 | 710 | 720 |
| GTGGAATTCC | TGCCGGTGCA | GGAAACGCAG | AATGATGCGA | ACGATGTGGT | TCCCAATTCA |
| 730 | 740 | 750 | 760 | 770 | 780 |
| GATGCCAACC | AGAACTACTG | GGGCTACATG | ACCGAGAACT | ACTTCTCGCC | GGATCGCCGC |
| 790 | 800 | 810 | 820 | 830 | 840 |
| TATGCCTACA | ACAAGGCGGC | TGGCGGTCCC | ACGGCGGAGT | TCCAGGCGAT | GGTGCAGGCG |
| 850 | 860 | 870 | 880 | 890 | 900 |
| TTTCACAACG | CAGGCATCAA | GGTCTACATG | GATGTGGTCT | ACAACCACAC | CGCCGAAGGC |

TABLE 1-1-continued

|  |  |  |  |  |  |
|---|---|---|---|---|---|
| 910 | 920 | 930 | 940 | 950 | 960 |
| GGCACCTGGA | CCAGCAGTGA | TCCCACCACG | GCCACCATTT | ATTCGTGGCG | CGGCTTGGAC |
| 970 | 980 | 990 | 1000 | 1010 | 1020 |
| AATGCCACGT | ACTACGAGCT | GACCTCGGGC | AACCAATACT | TCTACGACAA | CACGGGCATT |
| 1030 | 1040 | 1050 | 1060 | 1070 | 1080 |
| GGCGCGAACT | TCAATACGTA | CAACACGGTG | GCGCAGAACC | TTATCGTCGA | CTCGGTGGCG |
| 1090 | 1100 | 1110 | 1120 | 1130 | 1140 |
| TATTGGGCGA | ACACGATGGG | CGTGGATGGC | TTTCGCTTCG | ACCTTGCTTC | CGTGCTCGGC |
| 1150 | 1160 | 1170 | 1180 | 1190 | 1200 |
| AACAGTTGCC | TCAATGCCGT | ACACGCGTCC | GCGCCCAATT | GCCCGAACGG | TGGTTATAAC |
| 1210 | 1220 | 1230 | 1240 | 1250 | 1260 |
| TTCGACGCGG | CGGATAGCAA | CGTAGCGATC | AACCGCATCC | TACGCGAGTT | CACGGTGCGC |
| 1270 | 1280 | 1290 | 1300 | 1310 | 1320 |
| CCGGCGGCGG | GCGGCACGGT | CTGGATCTGT | TTGCGGAACC | TTGGGCCATC | GGCGGCAACT |
| 1330 | 1340 | 1350 | 1360 | 1370 | 1380 |
| CGTACCAGCT | GGGTGGATTC | CCGCAGGGTG | GTCCGAGTGG | AATGGTCTGT | TCCGCGACAG |
| 1390 | 1400 | 1410 | 1420 | 1430 | 1440 |
| CTGCGGCAGG | CGCAGAACGA | GCTGGGTAGC | ATGACCATCT | ATGTGACGCA | GGATGCGAAT |
| 1450 | 1460 | 1470 | 1480 | 1490 | 1500 |
| GATTTCTCCG | GTTCGTCCAA | TCTGTTCCAG | TCCAGTGGGC | GGTCGCCGTG | GAACTCGATC |
| 1510 | 1520 | 1530 | 1540 | 1550 | 1560 |
| AACTTTATCG | ACGTGCATGA | CGGCATGACG | TTGAAGGACG | TGTACTCCTG | CAACGGCGCC |
| 1570 | 1580 | 1590 | 1600 | 1610 | 1620 |
| AACAACAGTC | AGGCGTCGTA | CGGGCCGTCG | GATGGCGGCA | CGAGCACCAA | TTACAGTTGG |
| 1630 | 1640 | 1650 | 1660 | 1670 | 1680 |
| GATCAGGGCA | TGTCGGCGGG | AACGGGTGCC | GCGGTCGACC | AGCGTCGAGC | GGCACGAACG |
| 1690 | 1700 | 1710 | 1720 | 1730 | 1740 |
| GGCATGGCCT | TCGAGATGTT | GTCCGCGGGC | ACGCCGTTGA | TGCAGGGCGG | CGACGAATAC |
| 1750 | 1760 | 1770 | 1780 | 1790 | 1800 |
| CTGCGCACGC | TCCAGTGCAA | CAACAATGCC | TACAACCTCG | ACTCCAGCGC | CAACTGGCTT |
| 1810 | 1820 | 1830 | 1840 | 1850 | 1860 |
| ACCTATAGCT | GGACCACCGA | TCAATCGAAC | TTCTACACCT | TCGCGCAACG | CCTCATTCGT |
| 1870 | 1880 | 1890 | 1900 | 1910 | 1920 |
| TCCGCAAGGC | ACATCCCGCT | TCGCCCGTCG | AGCTGGTACA | GCGGCAGCCA | GTTGACGTGG |
| 1930 | 1940 | 1950 | 1960 | 1970 | 1980 |
| TATCAGCCCA | GTGGAGCCGT | GGCGGACAGC | AACTACTGGA | ACAACACCAG | CAACTACGCC |
| 1990 | 2000 | 2010 | 2020 | 2030 | 2040 |
| ATTGCCTACG | CCATCAATGG | GCCTTCGCTG | GGCGACAGCA | ATTCCATCTA | TGTCGCTTAC |
| 2050 | 2060 | 2070 | 2080 | 2090 | 2100 |
| AACGGTTGGT | CGAGCAGCGT | GACTTTCACC | TTGCCTGCGC | CACCGTCAGG | CACGCAGTGG |
| 2110 | 2120 | 2130 | 2140 | 2150 | 2160 |
| TATCGCGTCA | CGGATACCTG | CGACTGGAAC | GATGGCGCCA | GTACGTTTGT | TGCACCGGGC |
| 2170 | 2180 | 2190 | 2200 | 2210 | 2220 |
| AGCGAGACAT | TGATCGGCGG | CGCGGGCACC | ACCTATGGGC | AATGCGGTCA | ATCGCTGCTG |
| 2230 |  |  |  |  |  |
| CTGTTGATCT | CCAAG |  |  |  |  |

TABLE 1-2

|  |  |  |  |  |  |
|---|---|---|---|---|---|
| 10 | 20 | 30 | 40 | 50 | 60 |
| ATGAAGTGCC | CAAAGATTCT | CGGCGCGCTG | CTTGGCTGCG | CGGTGCTCGC | TGGTGTGCCC |
| 70 |  |  |  |  |  |
| GCAATGCCGG | CGCATGCG |  |  |  |  |

Experiment 3-(6)

Amino Acid Sequence of Polypeptide

The amino acid sequence of polypeptide was determined with reference to the sequence as shown in Table 1-1, and the results were as shown in Table 2-1.

The amino acid sequence of the signal peptide was determined in the same manner, and the results were as shown in Table 2-2.

These evidences confirmed that the polypeptide derived from *Pseudomonas amyloderamosa* SB-15 (ATCC 21262) has the amino acid sequence as shown in Table 2-1.

Unexpectedly, the results confirmed that the present polypeptide had an amino acid sequence corresponding to that of pullulanase, an enzyme that debranches pullulan.

The results were as shown in Table 3.

As evident from the results in Table 3, the present polypeptide has partial amino acid sequences similar to that of pullulanase, and it is estimated that the partial amino acid sequences are extremely relevant to the enzymatic activity on alpha-1,6-glucosidic linkages which is a common property of the present polypeptide and pullulanase.

It is also confirmed that the polypeptide has partial

TABLE 2-1

```
       1    2    3    4    5    6    7    8    9   10   11   12   13   14   15
  1> Ala—Ile—Asn—Ser—Met—Ser—Leu—Gly—Ala—Ser—Tyr—Asp—Ala—Gln—Gln—
 16> Ala—Asn—Ile—Thr—Phe—Arg—Val—Tyr—Ser—Ser—Gln—Ala—Thr—Arg—Ile—
 31> Val—Leu—Tyr—Leu—Tyr—Ser—Ala—Gly—Tyr—Gly—Val—Gln—Glu—Ser—Ala—
 46> Thr—Tyr—Thr—Leu—Ser—Pro—Ala—Gly—Ser—Gly—Val—Trp—Ala—Val—Thr—
 61> Val—Pro—Val—Ser—Ser—Ile—Lys—Ala—Ala—Gly—Ile—Thr—Gly—Ala—Val—
 76> Tyr—Tyr—Gly—Tyr—Arg—Ala—Trp—Gly—Pro—Asn—Trp—Pro—Tyr—Ala—Ser—
 91> Asn—Trp—Gly—Lys—Gly—Ser—Gln—Ala—Gly—Cys—Val—Ser—Asp—Val—Asp—
106> Ala—Asn—Gly—Asp—Arg—Phe—Asn—Pro—Asn—Lys—Leu—Leu—Leu—Asp—Pro—
121> Tyr—Ala—Gln—Glu—Val—Ser—Gln—Asp—Pro—Leu—Asn—Pro—Ser—Asn—Gln—
136> Asn—Gly—Asn—Val—Phe—Ala—Ser—Ala—His—Tyr—Arg—Thr—Thr—Asp—Ser—
151> Gly—Ile—Tyr—Ala—Pro—Lys—Gly—Val—Val—Leu—Val—Pro—Ser—Thr—Gln—
166> Ser—Thr—Gly—Thr—Lys—Pro—Thr—Arg—Ala—Gln—Lys—Asp—Asp—Val—Ile—
181> Tyr—Glu—Val—His—Val—Arg—Gly—Phe—Thr—Glu—Gln—Asp—Thr—Ser—Ile—
196> Pro—Ala—Gln—Tyr—Arg—Gly—Thr—Tyr—Tyr—Gly—Ala—Gly—Leu—Lys—Ala—
211> Ser—Tyr—Leu—Ala—Ser—Leu—Gly—Val—Thr—Ala—Val—Glu—Phe—Leu—Pro—
226> Val—Gln—Glu—Thr—Gln—Asn—Asp—Ala—Asn—Asp—Val—Val—Pro—Asn—Ser—
241> Asp—Ala—Asn—Gln—Asn—Tyr—Trp—Gly—Tyr—Met—Thr—Glu—Asn—Tyr—Phe—
256> Ser—Pro—Asp—Arg—Arg—Tyr—Ala—Tyr—Asn—Lys—Ala—Ala—Gly—Gly—Pro—
271> Thr—Ala—Glu—Phe—Gln—Ala—Met—Val—Gln—Ala—Phe—His—Asn—Ala—Gly—
286> Ile—Lys—Val—Tyr—Met—Asp—Val—Val—Tyr—Asn—His—Thr—Ala—Glu—Gly—
301> Gly—Thr—Trp—Thr—Ser—Ser—Asp—Pro—Thr—Thr—Ala—Thr—Ile—Tyr—Ser—
316> Trp—Arg—Gly—Leu—Asp—Asn—Ala—Thr—Tyr—Tyr—Glu—Leu—Thr—Ser—Gly—
331> Asn—Gln—Tyr—Phe—Tyr—Asp—Asn—Thr—Gly—Ile—Gly—Ala—Asn—Phe—Asn—
346> Thr—Tyr—Asn—Thr—Val—Ala—Gln—Asn—Leu—Ile—Val—Asp—Ser—Val—Ala—
361> Tyr—Trp—Ala—Asn—Thr—Met—Gly—Val—Asp—Gly—Phe—Arg—Phe—Asp—Leu—
376> Ala—Ser—Val—Leu—Gly—Asn—Ser—Cys—Leu—Asn—Ala—Val—His—Ala—Ser—
391> Ala—Pro—Asn—Cys—Pro—Asn—Gly—Gly—Tyr—Asn—Phe—Asp—Ala—Ala—Asp—
406> Ser—Asn—Val—Ala—Ile—Asn—Arg—Ile—Leu—Arg—Glu—Phe—Thr—Val—Arg—
421> Pro—Ala—Ala—Gly—Gly—Thr—Val—Trp—Ile—Cys—Leu—Arg—Asn—Leu—Gly—
436> Pro—Ser—Ala—Ala—Thr—Arg—Thr—Ser—Trp—Val—Asp—Ser—Arg—Arg—Val—
451> Val—Arg—Val—Glu—Trp—Ser—Val—Pro—Arg—Gln—Leu—Arg—Gln—Ala—Gln—
466> Asn—Glu—Leu—Gly—Ser—Met—Thr—Ile—Tyr—Val—Thr—Gln—Asp—Ala—Asn—
481> Asp—Phe—Ser—Gly—Ser—Ser—Asn—Leu—Phe—Gln—Ser—Ser—Gly—Arg—Ser—
496> Pro—Trp—Asn—Ser—Ile—Asn—Phe—Ile—Asp—Val—His—Asp—Gly—Met—Thr—
511> Leu—Lys—Asp—Val—Tyr—Ser—Lys—Asn—Gly—Ala—Asn—Asn—Ser—Gln—Ala—
526> Ser—Tyr—Gly—Pro—Ser—Asp—Gly—Gly—Thr—Ser—Thr—Asn—Tyr—Ser—Trp—
541> Asp—Gln—Gly—Met—Ser—Ala—Gly—Thr—Gly—Ala—Ala—Val—Asp—Gln—Arg—
556> Arg—Ala—Ala—Arg—Thr—Gly—Met—Ala—Phe—Glu—Met—Leu—Ser—Ala—Gly—
571> Thr—Pro—Leu—Met—Gln—Gly—Gly—Asp—Glu—Tyr—Leu—Arg—Thr—Leu—Gln—
586> Cys—Asn—Asn—Asn—Ala—Tyr—Asn—Leu—Asp—Ser—Ser—Ala—Asn—Trp—Leu—
601> Thr—Tyr—Ser—Trp—Thr—Thr—Asp—Gln—Ser—Asn—Phe—Tyr—Thr—Phe—Ala—
616> Gln—Arg—Leu—Ile—Arg—Ser—Ala—Arg—His—Ile—Pro—Leu—Arg—Pro—Ser—
631> Ser—Trp—Tyr—Ser—Gly—Ser—Gln—Leu—Thr—Trp—Tyr—Gln—Pro—Ser—Gly—
646> Ala—Val—Ala—Asp—Ser—Asn—Tyr—Trp—Asn—Asn—Thr—Ser—Asn—Tyr—Ala—
661> Ile—Ala—Tyr—Ala—Ile—Asn—Gly—Pro—Ser—Leu—Gly—Asp—Ser—Asn—Ser—
676> Ile—Tyr—Val—Ala—Tyr—Asn—Gly—Trp—Ser—Ser—Ser—Val—Thr—Phe—Thr—
691> Leu—Pro—Ala—Pro—Pro—Ser—Gly—Thr—Gln—Trp—Tyr—Arg—Val—Thr—Asp—
706> Thr—Cys—Asp—Trp—Asn—Asp—Gly—Ala—Ser—Thr—Phe—Val—Ala—Pro—Gly—
721> Ser—Glu—Thr—Leu—Ile—Gly—Gly—Ala—Gly—Thr—Thr—Tyr—Gly—Gln—Cys—
736> Gly—Gln—Ser—Leu—Leu—Leu—Leu—Ile—Ser—Lys
```

TABLE 2-2

Met—Lys—Cys—Pro—Lys—Ile—Leu—Gly—Ala—Leu—Leu—Gly—Cys—Ala—Val—
Leu—Ala—Gly—Val—Pro—Ala—Met—Pro—Ala—His—Ala

The amino acid sequence was compared with that of a pullulanase possessing starch debranching activity described in *Journal of Bacteriology*, Vol. 169, No. 5, pp. 2301–2306 (1987).

amino acid sequences of (a) Met—Asp—Val—Val—Tyr—Asn—His—Thr and (b) Asp—Gly—Phe—Arg—Phe—Asp—Leu which are located in this order from the N-terminal of the polypeptide.

TABLE 3

| Enzymes | Common amino acid sequences (a) | (b) |
|---|---|---|
| Isoamylase | 289<br>Met—Asp—Val—Val—Tyr—Asn—His—Thr | 369<br>Asp—Gly—Phe—Arg—Phe—Asp—Leu |
| Pullulanase | 599<br>Met—Asp—Val—Val—Tyr—Asn—His—Thr | 670<br>Asp—Gly—Phe—Arg—Phe—Asp—Leu |

Experiment 4

Preparation of Polypeptide with Transformed Microorganism

The polypeptide productivities of a transformed microorganism of *Escherichia coli* IAM275, in which a recombinant DNA carrying polypeptide gene derived from *Pseudomonas amyloderamosa* SB-15 (ATCC 21262), the host microorganism *Escherichia coli* JM83, and the donor microorganism *Pseudomonas amyloderamosa* SB-15 (ATCC 21262) were compared in terms of polypeptide activities. A liquid culture medium containing 2 w/v % maltose, 0.4 w/v % sodium glutamate, 0.2 w/v % corn steep liquor, 0.1 w/v % polypeptone, 0.1 w/v % ammonium phosphate, 0.1 w/v % dipotassium hydrogen phosphate, 0.05 w/v % magnesium sulfate hepta hydrate, and water was adjusted to pH 7.0, sterilized by heating at 120° C. for 20 minutes, and cooled.

In the case of *Escherichia coli* IAM275, it was inoculated to the liquid culture medium with 50 μg/ml of ampicillin, while that of *Escherichia coli* JM83, it was inoculated to the liquid culture medium without antibiotic. In each case, the microorganism was cultured at 37° C. for 24 hours under agitation-aeration conditions.

Separately, a seed culture of *Pseudomonas amyloderamosa* SB-15 (ATCC 21262) was inoculated to the liquid culture medium without addition of antibiotic, and cultured at 28° C. for 24- and 96-hours. After centrifugal separation of each liquid culture medium into a supernatant and a cell, the isoamylase activity of the supernatant was assayed without further preparation. The cell was ultrasonically homogenized, prior to its assay, and its isoamylase activity was determined based on the activity per volume of the liquid culture medium.

The results were as shown in Table 4.

TABLE 4

| Microorganism | Isoamylase activity (units/ml) Supernatant | Cell | Total | Incubation period (hours) |
|---|---|---|---|---|
| *Escherichia coli* IAM275 | 5 | 305 | 310 | 24 |
| *Escherichia coli* JM83 | 0 | 0 | 0 | 24 |
| *Pseudomonas amyloderamosa* SB-15 | 50 | 15 | 65 | 24 |
| *Pseudomonas amyloderamosa* SB-15 | 127 | 9 | 136 | 96 |

As evident from the results in Table 4, the transformed microorganism is advantageously usable in industrial-scale production of polypeptide because the transformed microorganism possesses an improved polypeptide productivity.

Several embodiments and effects of the present invention will hereinafter be explained.

Example 1

Polypeptide

Fifteen liters of a liquid culture medium containing 2 w/v % maltose, 0.1 w/v % sodium glutamate, 1.0 w/v % corn steep liquor, 0.5 w/v % polypeptone, 0.2 w/v % ammonium nitrate, 0.2 w/v % dipotassium hydrogen phosphate, 0.05 w/v % magnesium sulfate hepta hydrate, and water was placed in a 30-liter jar fermentor, adjusted to pH 7.0, sterilized by heating at 120° C. for 20 minutes, and cooled. The liquid culture medium was added with 50 μg/ml of ampicillin, and 1 v/v % of a seed culture of *Escherichia coli* IAM275 was inoculated to the liquid culture medium, and cultured at 37° C. for 24 hours under agitation-aeration conditions. The activity of isoamylase in the resultant culture was about 380 units/ml. Cells, obtained from the resultant culture, were subjected to ultrasonic and centrifugation to obtain a supernatant which was then purified by the method in Experiment 2-(1) to obtain a solution containing high-purity polypeptide.

The solution containing polypeptide can be advantageously used in a preparation of a high-maltose content product from amylaceous substances.

The polypeptide was shown to have a molecular weight of 80,000±5,000 daltons on SDS-polyacrylamide gel electrophoresis and an isoelectric point of 4.7±0.1 on polyacrylamide gel isoelectric electrophoresis. Additionally, when incubated in 0.1M acetate buffer at different temperatures in the range of 30°-70° C. for 10 minutes, it was shown to be stable up to 50° C. and 70% of its activity was retained even when incubated at 55° C.

EXAMPLE 2

High-maltose content product

A suspension solution of 3 parts by weight of corn starch and 10 parts by weight of water was added with a commercialized alpha-amylase derived from a microorganism, and gelatinized at 90° C. The resultant mixture was heated to 130° C. to suspend the enzymatic reaction, and a liquefied solution having a dextrose equivalent (DE) of about 3 was obtained which was then cooled to 55° C., added with 100 units/g starch of a polypeptide solution obtained by the method in Example 1 together with 30 units/g starch of a beta-amylase derived from soybean, and saccharized at pH 5.0 for 36 hours. The resultant saccharized solution was decolored with an activated charcoal, deionized with ion-exchange resin, concentrated and added with a seed crystal to effect crystalization. Thereafter, the resultant was allowed to stand for 5 days to effect solidification. The product was pulverized into a high-maltose content powder containing 2.6% glucose, 85.4% maltose, 7.4% other dextrins in the yield of about 97%, dry solid basis.

The product can be extensively used in food products as a sweetener with a moderate sweetness.

Effect of the Invention

As evident from the above, the present invention relates to an elucidation of amino acid sequence of a polypeptide, as well as to a process for preparing a high-maltose content product from amylaceous substances using the polypeptide.

The present inventors elucidated that polypeptide has a great significance in the field because the polypeptide smoothly hydrolyzes amylaceous substances.

Furthermore, the present inventors elucidated that a microorganism of the species *Pseudomonas amyloderamosa* which possesses polypeptide producibility, as well as that a transformed microorganism in which the polypeptide gene has been introduced by genetic engineering technique in vitro, can be used as a polypeptide producer. The elucidation has a great significance in industrial uses because the present invention can ensure the extensive variety of polypeptide producers, as well as facilitating the improvement of the polypeptide producibility.

While there has been described what is at present considered to be the preferred embodiments of the invention, it will be understood that various modifications may be made therein, and it is intended to cover in the appended claims all such modifications as fall within the true spirit and scope of the invention.

We claim:

1. A process for preparing a high-maltose content product, which comprises:

hydrolyzing an amylaceous substance at a temperature not lower than 50° C. with a beta-amylase and a polypeptide obtainable from *Pseudomonas amyloderamosa* possessing isoamylase activity which hydrolyzes alpha-1,6-glucosidic linkages of starch and glycogen, said polypeptide having an N-terminal sequence of Ala—Ile—Asn—Ser—Met—Ser—Leu—Gly—Ala—Ser—Tyr—Asp—Ala—Gln—Gln—Ala—Asn—Ile—Thr—Phe and including within its sequence each of the following partial amino acid sequences;

a) Met—Asp—Val—Val—Tyr—Asn—His—Thr, and b) Asp—Gly—Phe—Arg—Phe—Asp—Leu, the initial amino acid (a) being located closer to the N-terminal of said polypeptide than that of (b), said polypeptide having the following physicochemical properties:

c) molecular weight: 80,000±5,000 daltons on SDS-polyacrylamide gel electrophoresis;

d) isoelectric point: 4.7±0.1 on polyacrylamide gel isoelectric electrophoresis; and e) thermal stability:

stable up to 50° C. when incubated in 0.1M acetate buffer (pH 3.5) for 10 minutes to produce a high-maltose content product; and recovering the resultant high-maltose content product.

2. The process as claimed in claim 1, wherein said polypeptide is derived from a microorganism capable of producing isoamylase which hydrolyzes alpha-1,6-linkages of starch and glycogen.

3. The process as claimed in claim 2, wherein said microorganism is a microorganism of the species *Pseudomonas amyloderamosa*.

4. The process as claimed in claim 1, wherein said polypeptide has an amino acid sequence of

```
        1    2    3    4    5    6    7    8    9   10   11   12   13   14   15
  1> Ala—Ile—Asn—Ser—Met—Ser—Leu—Gly—Ala—Ser—Tyr—Asp—Ala—Gln—Gln—
 16> Ala—Asn—Ile—Thr—Phe—Arg—Val—Tyr—Ser—Ser—Gln—Ala—Thr—Arg—Ile—
 31> Val—Leu—Tyr—Leu—Tyr—Ser—Ala—Gly—Tyr—Gly—Val—Gln—Glu—Ser—Ala—
 46> Thr—Tyr—Thr—Leu—Ser—Pro—Ala—Gly—Ser—Gly—Val—Trp—Ala—Val—Thr—
 61> Val—Pro—Val—Ser—Ser—Ile—Ala—Gly—Ile—Thr—Gly—Ala—Val—
 76> Tyr—Tyr—Gly—Tyr—Arg—Ala—Trp—Gly—Pro—Asn—Trp—Pro—Tyr—Ala—Ser—
 91> Asn—Trp—Gly—Lys—Gly—Ser—Gln—Ala—Gly—Cys—Val—Ser—Asp—Val—Asp—
106> Ala—Asn—Gly—Asp—Arg—Phe—Asn—Pro—Asn—Lys—Leu—Leu—Leu—Asp—Pro—
121> Tyr—Ala—Gln—Glu—Val—Ser—Gln—Asp—Pro—Leu—Asn—Pro—Ser—Asn—Gln—
136> Asn—Gly—Asn—Val—Phe—Ala—Ser—Ala—His—Tyr—Arg—Thr—Thr—Asp—Ser—
151> Gly—Ile—Tyr—Ala—Pro—Lys—Gly—Val—Val—Leu—Val—Pro—Ser—Thr—Gln—
166> Ser—Thr—Gly—Thr—Lys—Pro—Thr—Arg—Ala—Gln—Lys—Asp—Asp—Val—Ile—
181> Tyr—Glu—Val—His—Val—Arg—Gly—Phe—Thr—Glu—Gln—Asp—Thr—Ser—Ile—
196> Pro—Ala—Gln—Tyr—Arg—Gly—Thr—Tyr—Tyr—Gly—Ala—Gly—Leu—Lys—Ala—
211> Ser—Tyr—Leu—Ala—Ser—Leu—Gly—Val—Thr—Ala—Val—Glu—Phe—Leu—Pro—
226> Val—Gln—Glu—Thr—Gln—Asn—Asp—Ala—Asn—Asp—Val—Val—Pro—Asn—Ser—
241> Asp—Ala—Asn—Gln—Asn—Tyr—Trp—Gly—Tyr—Met—Thr—Glu—Asn—Tyr—Phe—
256> Ser—Pro—Asp—Arg—Arg—Tyr—Ala—Tyr—Asn—Lys—Ala—Ala—Gly—Gly—Pro—
271> Thr—Ala—Glu—Phe—Gln—Ala—Met—Val—Gln—Ala—Phe—His—Asn—Ala—Gly—
286> Ile—Lys—Val—Tyr—Met—Asp—Val—Val—Tyr—Asn—His—Thr—Ala—Glu—Gly—
301> Gly—Thr—Trp—Thr—Ser—Ser—Asp—Pro—Thr—Thr—Ala—Thr—Ile—Tyr—Ser—
316> Trp—Arg—Gly—Leu—Asp—Asn—Ala—Thr—Tyr—Tyr—Glu—Leu—Thr—Ser—Gly—
331> Asn—Gln—Tyr—Phe—Tyr—Asp—Asn—Thr—Gly—Ile—Gly—Ala—Asn—Phe—Asn—
346> Thr—Tyr—Asn—Thr—Val—Ala—Gln—Asn—Leu—Ile—Val—Asp—Ser—Val—Ala—
361> Tyr—Trp—Ala—Asn—Thr—Met—Gly—Val—Asp—Gly—Phe—Arg—Phe—Asp—Leu—
376> Ala—Ser—Val—Leu—Gly—Asn—Ser—Cys—Leu—Asn—Ala—Val—His—Ala—Ser—
391> Ala—Pro—Asn—Cys—Pro—Asn—Gly—Gly—Tyr—Asn—Phe—Asp—Ala—Ala—Asp—
406> Ser—Asn—Val—Ala—Ile—Asn—Arg—Ile—Leu—Arg—Glu—Phe—Thr—Val—Arg—
421> Pro—Ala—Ala—Gly—Gly—Thr—Val—Trp—Ile—Cys—Leu—Arg—Asn—Leu—Gly—
436> Pro—Ser—Ala—Ala—Thr—Arg—Thr—Ser—Trp—Val—Asp—Ser—Arg—Arg—Val—
451> Val—Arg—Val—Glu—Trp—Ser—Val—Pro—Arg—Gln—Leu—Arg—Gln—Ala—Gln—
466> Asn—Glu—Leu—Gly—Ser—Met—Thr—Ile—Tyr—Val—Thr—Gln—Asp—Ala—Asn—
481> Asp—Phe—Ser—Gly—Ser—Ser—Asn—Leu—Phe—Gln—Ser—Ser—Gly—Arg—Ser—
496> Pro—Trp—Asn—Ser—Ile—Asn—Phe—Ile—Asp—Val—His—Asp—Gly—Met—Thr—
511> Leu—Lys—Asp—Val—Tyr—Ser—Lys—Asn—Gly—Ala—Asn—Asn—Ser—Gln—Ala—
526> Ser—Tyr—Gly—Pro—Ser—Asp—Gly—Gly—Thr—Ser—Thr—Asn—Tyr—Ser—Trp—
541> Asp—Gln—Gly—Met—Ser—Ala—Gly—Thr—Gly—Ala—Ala—Val—Asp—Gln—Arg—
```

```
556>  Arg—Ala—Ala—Arg—Thr—Gly—Met—Ala—Phe—Glu—Met—Leu—Ser—Ala—Gly—
571>  Thr—Pro—Leu—Met—Gln—Gly—Gly—Asp—Glu—Tyr—Leu—Arg—Thr—Leu—Gln—
586>  Cys—Asn—Asn—Asn—Ala—Tyr—Asn—Leu—Asp—Ser—Ser—Ala—Asn—Trp—Leu—
601>  Thr—Tyr—Ser—Trp—Thr—Thr—Asp—Gln—Ser—Asn—Phe—Tyr—Thr—Phe—Ala—
616>  Gln—Arg—Leu—Ile—Arg—Ser—Ala—Arg—His—Ile—Pro—Leu—Arg—Pro—Ser—
631>  Ser—Trp—Tyr—Ser—Gly—Ser—Gln—Leu—Thr—Trp—Tyr—Gln—Pro—Ser—Gly—
646>  Ala—Val—Ala—Asp—Ser—Asn—Tyr—Trp—Asn—Asn—Thr—Ser—Asn—Tyr—Ala—
661>  Ile—Ala—Tyr—Ala—Ile—Asn—Gly—Pro—Ser—Leu—Gly—Asp—Ser—Asn—Ser—
676>  Ile—Tyr—Val—Ala—Tyr—Asn—Gly—Trp—Ser—Ser—Ser—Val—Thr—Phe—Thr—
691>  Leu—Pro—Ala—Pro—Pro—Ser—Gly—Thr—Gln—Trp—Tyr—Arg—Val—Thr—Asp—
706>  Thr—Cys—Asp—Trp—Asn—Asp—Gly—Ala—Ser—Thr—Phe—Val—Ala—Pro—Gly—
721>  Ser—Glu—Thr—Leu—Ile—Gly—Gly—Ala—Gly—Thr—Thr—Tyr—Gly—Gln—Cys—
736>  Gly—Gln—Ser—Leu—Leu—Leu—Leu—Ile—Ser—Lys
```

5. An isolated polypeptide obtainable from *Pseudomonas amyloderamosa* possessing isoamylase activity which hydrolyzes alpha-1,6-glucosidic linkages of starch and glycogen, said polypeptide having an N-terminal sequence of Ala—Ile—Asn—Ser—Met—Ser—Leu—Gly—Ala—Ser—Tyr—Asp—Ala—Gla—Gln—Ala—Asn—Ile—Thr—Phe and including within its sequence each of the following partial amino acid sequences:

a) Met—Asp—Val—Val—Tyr—Asn—His—Thr, and b) Asp—Gly—Phe—Arg—Phe—Asp—Leu, the initial amino acid (a) being located closer to the N-terminal of said polypeptide than that of (b), said polypeptide having the following physicochemical properties:

c) molecular weight: 80,000±5,000 daltons on SDS-polyacrylamide gel electrophoresis;

d) isoelectric point: 4.7±0.1 on polyacrylamide gel isoelectric electrophoresis; and e) thermal stability: stable up to 50° C. when incubated in 0.1M acetate buffer (pH 3.5) for 10 minutes.

6. The polypeptide is claimed in claim 5, wherein said polypeptide is derived from a microorganism capable of producing isoamylase which hydrolyzes alpha-1,6-linkages of starch and glycogen.

7. The polypeptide as claimed in claim 6, wherein said microorganism is a microorganism of the species *Pseudomonas amyloderamosa*.

8. The polypeptide as claimed in claim 5, wherein said polypeptide has an amino acid sequence of

```
         1    2    3    4    5    6    7    8    9   10   11   12   13   14   15
  1>  Ala—Ile—Asn—Ser—Met—Ser—Leu—Gly—Ala—Ser—Tyr—Asp—Ala—Gln—Gln—
 16>  Ala—Asn—Ile—Thr—Phe—Arg—Val—Tyr—Ser—Ser—Gln—Ala—Thr—Arg—Ile—
 31>  Val—Leu—Tyr—Leu—Tyr—Ser—Ala—Gly—Tyr—Gly—Val—Gln—Glu—Ser—Ala—
 46>  Thr—Tyr—Thr—Leu—Ser—Pro—Ala—Gly—Ser—Gly—Val—Trp—Ala—Val—Thr—
 61>  Val—Pro—Val—Ser—Ser—Ile—Lys—Ala—Ala—Gly—Ile—Thr—Gly—Ala—Val—
 76>  Tyr—Tyr—Gly—Tyr—Arg—Ala—Trp—Gly—Pro—Asn—Trp—Pro—Tyr—Ala—Ser—
 91>  Asn—Trp—Gly—Lys—Gly—Ser—Gln—Ala—Gly—Cys—Val—Ser—Asp—Val—Asp—
106>  Ala—Asn—Gly—Asp—Arg—Phe—Asn—Pro—Asn—Lys—Leu—Leu—Leu—Asp—Pro—
121>  Tyr—Ala—Gln—Glu—Val—Ser—Gln—Asp—Pro—Leu—Asn—Pro—Ser—Asn—Gln—
136>  Asn—Gly—Asn—Val—Phe—Ala—Ser—Ala—His—Tyr—Arg—Thr—Thr—Asp—Ser—
151>  Gly—Ile—Tyr—Ala—Pro—Lys—Gly—Val—Val—Leu—Val—Pro—Ser—Thr—Gln—
166>  Ser—Thr—Gly—Thr—Lys—Pro—Thr—Arg—Ala—Gln—Lys—Asp—Asp—Val—Ile—
181>  Tyr—Glu—Val—His—Val—Arg—Gly—Phe—Thr—Gln—Gln—Asp—Thr—Ser—Ile—
196>  Pro—Ala—Gln—Tyr—Arg—Gly—Thr—Tyr—Tyr—Gly—Ala—Gly—Leu—Lys—Ala—
211>  Ser—Tyr—Leu—Ala—Ser—Leu—Gly—Val—Thr—Ala—Val—Glu—Phe—Leu—Pro—
226>  Val—Gln—Glu—Thr—Gln—Asn—Asp—Ala—Asn—Asp—Val—Val—Pro—Asn—Ser—
241>  Asp—Ala—Asn—Gln—Asn—Tyr—Trp—Gly—Tyr—Met—Thr—Glu—Asn—Tyr—Phe—
256>  Ser—Pro—Asp—Arg—Arg—Tyr—Ala—Tyr—Asn—Lys—Ala—Ala—Gly—Gly—Pro—
271>  Thr—Ala—Glu—Phe—Gln—Ala—Met—Val—Gln—Ala—Phe—His—Asn—Ala—Gly—
286>  Ile—Lys—Val—Tyr—Met—Asp—Val—Val—Tyr—Asn—His—Thr—Ala—Glu—Gly—
301>  Gly—Thr—Trp—Thr—Ser—Ser—Asp—Pro—Thr—Thr—Ala—Thr—Ile—Tyr—Ser—
316>  Trp—Arg—Gly—Leu—Asp—Asn—Ala—Thr—Tyr—Tyr—Glu—Leu—Thr—Ser—Gly—
331>  Asn—Gln—Tyr—Phe—Tyr—Asp—Asn—Thr—Gly—Ile—Gly—Ala—Asn—Phe—Asn—
346>  Thr—Tyr—Asn—Thr—Val—Ala—Gln—Asn—Leu—Ile—Val—Asp—Ser—Val—Ala—
361>  Tyr—Trp—Ala—Asn—Thr—Met—Gly—Val—Asp—Gly—Phe—Arg—Phe—Asp—Leu—
376>  Ala—Ser—Val—Leu—Gly—Asn—Ser—Cys—Leu—Asn—Ala—Val—His—Ala—Ser—
391>  Ala—Pro—Asn—Cys—Pro—Asn—Gly—Gly—Tyr—Asn—Phe—Asp—Ala—Ala—Asp—
406>  Ser—Asn—Val—Ala—Ile—Asn—Arg—Ile—Leu—Arg—Glu—Phe—Thr—Val—Arg—
421>  Pro—Ala—Ala—Gly—Gly—Thr—Val—Trp—Ile—Cys—Leu—Arg—Asn—Leu—Gly—
436>  Pro—Ser—Ala—Ala—Thr—Arg—Thr—Ser—Trp—Val—Asp—Ser—Arg—Arg—Val—
451>  Val—Arg—Val—Glu—Trp—Ser—Val—Pro—Arg—Gln—Leu—Arg—Gln—Ala—Gln—
466>  Asn—Glu—Leu—Gly—Ser—Met—Thr—Ile—Tyr—Val—Thr—Gln—Asp—Ala—Asn—
481>  Asp—Phe—Ser—Gly—Ser—Ser—Asn—Leu—Phe—Gln—Ser—Ser—Gly—Arg—Ser—
496>  Pro—Trp—Asn—Ser—Ile—Asn—Phe—Ile—Asp—Val—His—Asp—Gly—Met—Thr—
511>  Leu—Lys—Asp—Val—Tyr—Ser—Lys—Asn—Gly—Ala—Asn—Asn—Ser—Gln—Ala—
526>  Ser—Tyr—Gly—Pro—Ser—Asp—Gly—Gly—Thr—Ser—Thr—Asn—Tyr—Ser—Trp—
541>  Asp—Gln—Gly—Met—Ser—Ala—Gly—Thr—Gly—Ala—Ala—Val—Asp—Gln—Arg—
556>  Arg—Ala—Ala—Arg—Thr—Gly—Met—Ala—Phe—Glu—Met—Leu—Ser—Ala—Gly—
571>  Thr—Pro—Leu—Met—Gln—Gly—Gly—Asp—Glu—Tyr—Leu—Arg—Thr—Leu—Gln—
586>  Cys—Asn—Asn—Asn—Ala—Tyr—Asn—Leu—Asp—Ser—Ser—Ala—Asn—Trp—Leu—
601>  Thr—Tyr—Ser—Trp—Thr—Thr—Asp—Gln—Ser—Asn—Phe—Tyr—Thr—Phe—Ala—
616>  Gln—Arg—Leu—Ile—Arg—Ser—Ala—Arg—His—Ile—Pro—Leu—Arg—Pro—Ser—
631>  Ser—Trp—Tyr—Ser—Gly—Ser—Gln—Leu—Thr—Trp—Tyr—Gln—Pro—Ser—Gly—
646>  Ala—Val—Ala—Asp—Ser—Asn—Tyr—Trp—Asn—Asn—Thr—Ser—Asn—Tyr—Ala—
661>  Ile—Ala—Tyr—Ala—Ile—Asn—Gly—Pro—Ser—Leu—Gly—Asp—Ser—Asn—Ser—
676>  Ile—Tyr—Val—Ala—Tyr—Asn—Gly—Trp—Ser—Ser—Ser—Val—Thr—Phe—Thr—
```

-continued

691> Leu—Pro—Ala—Pro—Pro—Ser—Gly—Thr—Gln—Trp—Tyr—Arg—Val—Thr—Asp—
706> Thr—Cys—Asp—Trp—Asn—Asp—Gly—Ala—Ser—Thr—Phe—Val—Ala—Pro—Gly—
721> Ser—Glu—Thr—Leu—Ile—Gly—Gly—Ala—Gly—Thr—Thr—Tyr—Gly—Gln—Cys—
736> Gly—Gln—Ser—Leu—Leu—Leu—Leu—Ile—Ser—Lys

* * * * *